(12) United States Patent
Persson

(10) Patent No.: US 10,314,692 B2
(45) Date of Patent: Jun. 11, 2019

(54) VOICE PROSTHESIS

(71) Applicant: Atos Medical AB, Horby (SE)

(72) Inventor: Jan-Ove Persson, Hoor (SE)

(73) Assignee: Atos Medical AB (SE)

( * ) Notice: Subject to any disclaimer, the term of this patent is extended or adjusted under 35 U.S.C. 154(b) by 0 days.

(21) Appl. No.: 14/651,148

(22) PCT Filed: Nov. 22, 2013

(86) PCT No.: PCT/EP2013/074475
§ 371 (c)(1),
(2) Date: Jun. 10, 2015

(87) PCT Pub. No.: WO2014/090548
PCT Pub. Date: Jun. 19, 2014

(65) Prior Publication Data
US 2015/0327993 A1 Nov. 19, 2015

(30) Foreign Application Priority Data

Dec. 11, 2012 (SE) ...................... 1251403

(51) Int. Cl.
*A61F 2/20* (2006.01)
(52) U.S. Cl.
CPC ........ *A61F 2/203* (2013.01); *A61F 2210/009* (2013.01); *A61F 2220/005* (2013.01); *A61F 2230/0069* (2013.01); *A61F 2230/0086* (2013.01); *A61F 2250/006* (2013.01); *A61F 2250/0069* (2013.01)

(58) Field of Classification Search
CPC ...... A61F 2/20; A61F 2/203; A61F 2002/044; A61F 2002/046; A61F 2002/206
See application file for complete search history.

(56) References Cited

U.S. PATENT DOCUMENTS 3,370,305 A * 2/1968 Goott .................... A61F 2/2403
137/527
4,538,607 A * 9/1985 Saul .................. A61M 16/0468
128/207.16
(Continued)

FOREIGN PATENT DOCUMENTS

DE 20310919 U1 8/2004
EP 0299705 A2 1/1989
(Continued)

OTHER PUBLICATIONS

English translationof of JP Office Action for JP-2018-044252, dated Jan. 9, 2019.
English abstract for JP-H01-086966.

*Primary Examiner* — Andrew M Iwamaye
(74) *Attorney, Agent, or Firm* — Fishman Stewart PLLC

(57) ABSTRACT

A voice prosthesis for mounting in a fistula between trachea and esophagus is provided. The voice prosthesis comprises a tubular body having a lumen, a valve disc and a valve seat. The valve disc and a valve seat are arranged in the lumen of the tubular body, such that the valve disc and the valve seat control the connection through the lumen by interaction between the valve disc and the valve seat. A sealing rim is arranged between the valve disc and the valve seat, such that the interaction between the valve disc and the valve seat is obtained via the rim. A method for manufacturing a voice prosthesis is also provided.

20 Claims, 2 Drawing Sheets

(56) References Cited

U.S. PATENT DOCUMENTS

| | | | | |
|---|---|---|---|---|
| 4,820,304 A | * | 4/1989 | Depel | A61M 16/0468 |
| | | | | 623/9 |
| 4,911,716 A | * | 3/1990 | Blom | A61F 2/203 |
| | | | | 128/200.26 |
| 5,064,433 A | * | 11/1991 | Blom | A61F 2/203 |
| | | | | 128/207.16 |
| 5,103,854 A | * | 4/1992 | Bailey | A61M 16/208 |
| | | | | 128/205.24 |
| 5,578,083 A | * | 11/1996 | Laguette | A61F 2/203 |
| | | | | 137/855 |
| 7,166,128 B1 | | 1/2007 | Persson | |
| 2004/0123868 A1 | * | 7/2004 | Rutter | A61M 16/0468 |
| | | | | 128/207.14 |
| 2004/0187941 A1 | | 9/2004 | Seder et al. | |
| 2006/0276893 A1 | * | 12/2006 | Nelson | A61F 2/203 |
| | | | | 623/9 |
| 2006/0287722 A1 | * | 12/2006 | Nelson | A61F 2/203 |
| | | | | 623/9 |
| 2009/0026660 A1 | * | 1/2009 | Nelson | A61F 2/203 |
| | | | | 264/331.13 |
| 2015/0327993 A1 | | 11/2015 | Persson | |

FOREIGN PATENT DOCUMENTS

| | | | | |
|---|---|---|---|---|
| EP | 1504731 A1 | * | 2/2005 | A61F 2/20 |
| EP | 1733703 A1 | | 12/2006 | |
| JP | 2015-536219 A | | 12/2015 | |
| WO | WO 9726845 A1 | * | 7/1997 | A61F 2/203 |

\* cited by examiner

VOICE PROSTHESIS

CROSS-REFERENCE TO RELATED APPLICATIONS

This application claims priority to International Patent Application PCT/EP2013/074475 filed Nov. 22, 2013 and Swedish Patent Application No. 1251403-0 filed Dec. 11, 2012, the contents of which are hereby incorporated by reference in their entirety.

TECHNICAL FIELD

The present invention relates to a voice prosthesis to be mounted in a fistula between trachea and esophagus. More particularly, the invention relates to a voice prosthesis, comprising a tubular body, with a distal and a proximal end, wherein retention flanges are arranged to extend laterally in a transversal plane from the tubular body, said flanges being arranged at the proximal and the distal end, respectively, the voice prosthesis further comprising a valve member for closing the communication through the tubular body but opens when subjected to air flow in the proximal direction. The invention also relates to a method for manufacturing such voice prosthesis.

BACKGROUND

When a person's larynx has been removed by surgery due to pathological changes in the throat, the trachea of the person is sutured to an opening in the throat. This is called a tracheostoma. By the surgery the person has lost the ability to speak, and in order to restore this ability a voice prosthesis of the kind referred to above is mounted in a fistula, i.e. a passage between trachea and esophagus. At speech the tracheostoma is occluded by sealing the same either by the patient placing the fingers against the tracheostoma or by the tracheostoma being closed via a tracheostoma valve arranged in connection with the tracheostoma valve. Then, the expiration air is pressed from the lungs through the voice prosthesis into esophagus. Here the mucous membranes of the throat of the person are brought into vibration and speech is produced as a consequence thereof.

Existing voice prostheses have in common that they normally provide a check valve function, which means that the valve member normally is closed but opens when air is pressed from trachea via the valve member to esophagus. The valve member is maintained in the closed position by spring bias which in most cases is maintained by elasticity of the material from which the voice prosthesis is made.

The function of such voice prostheses is initially acceptable, but they tend to have short life span, since growth of candida most often occurs at the sealing surfaces of the valve member and the corresponding valve seat, causing leakage from the esophagus into the trachea, and the spring bias is lost, also this resulting in a leakage through the voice prosthesis from the esophagus into the trachea.

U.S. Pat. No. 7,166,128 discloses a voice prosthesis of this kind, wherein a permanent magnet is arranged at the valve member or the valve seat, and a permanently magnetically attracting material is arranged on the opposite side, i.e. the one of the valve member and the valve seat not being provided with the permanent magnet, to alleviate the problem of lost spring bias. The problem of candida formation is alleviated with the use of a candida resistant material on the valve member. However, since candida still will be formed adjacent the valve member and on the valve seat, as well as to some degree accumulate on the valve member, even though it does not grow into the candida resistant material, the valve member will not be able to close entirely against the valve seat, regardless of magnetic attraction between the valve member and the valve seat. Also, candida formed in the vicinity of the valve/valve seat may en up at the valve/valve seat, together with mucus, food, etc., which may cause a leakage until it is removed.

SUMMARY

Accordingly, the present invention preferably seeks to mitigate, alleviate or eliminate one or more of the above-identified deficiencies in the art and disadvantages singly or in any combination and solves at least the above mentioned problems by providing a voice prosthesis for mounting in a fistula between trachea and esophagus, comprising: a tubular body having a lumen; a valve disc and a valve seat, arranged in the lumen of the tubular body, said valve disc and said valve seat controlling the connection through said lumen by interaction between said valve disc and said valve seat; wherein a sealing rim is arranged between said valve disc and said valve seat, such that the interaction between said valve disc and said valve seat is obtained via said rim, and a method for manufacturing a voice prosthesis.

Advantageous features of the invention are defined in the dependent claims.

BRIEF DESCRIPTION OF THE DRAWINGS

These and other aspects, features and advantages of which the invention is capable of will be apparent and elucidated from the following description of embodiments of the present invention, reference being made to the accompanying drawings, in which.

DETAILED DESCRIPTION

The following description focuses on an embodiment of the present invention applicable to a voice prosthesis, and also to a method for manufacturing such a voice prosthesis.

Figure 1:
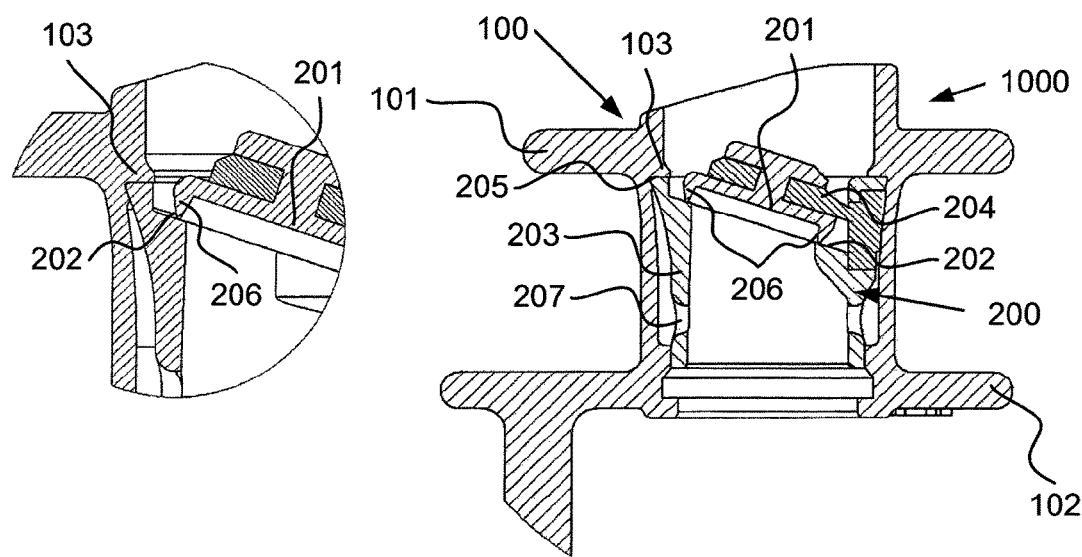
FIG. 1 is a cross sectional view, along the central axis, of a voice prosthesis according to one embodiment of the present invention.
Figure 2:
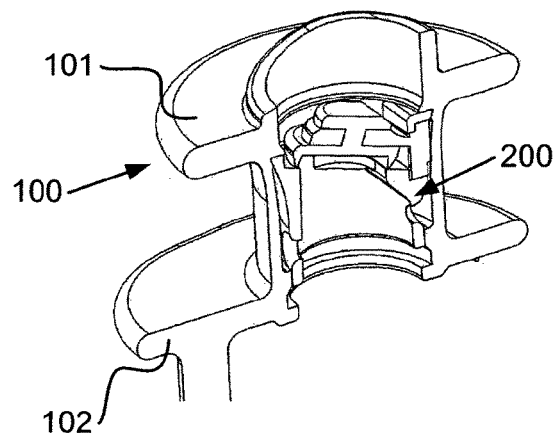
FIG. 2 is a perspective and cross sectional view of a voice prosthesis according to one embodiment of the present invention.
Figure 3:
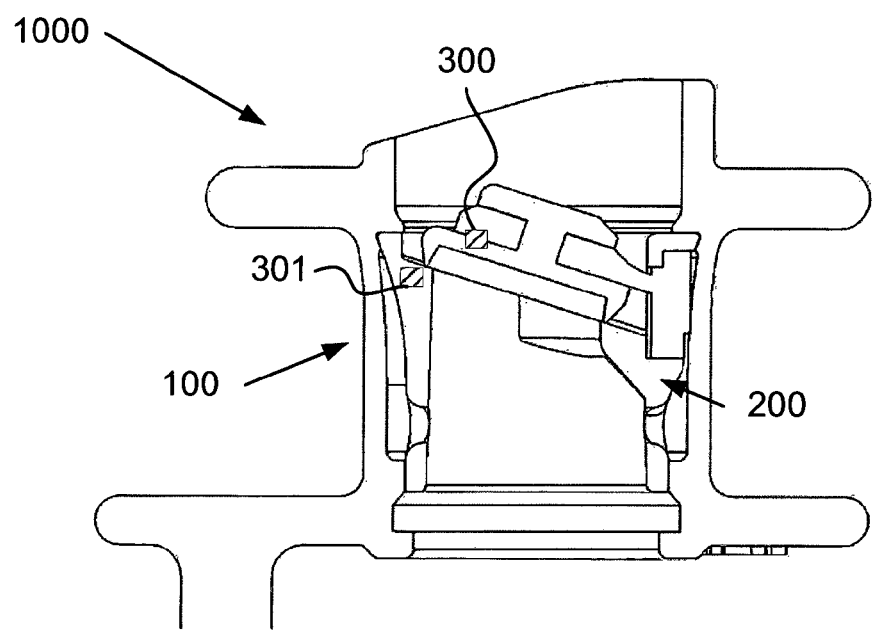
FIG. 3 is a cross sectional view, along the central axis, of a voice prosthesis according to one embodiment of the present invention.

The invention will be described in more detail below reference being made to the accompanying drawings in which FIGS. 1 to 3 are axial cross-sectional views, as well as perspective cross sectional views of different embodiments of the voice prosthesis 1000 according to the invention.

In an embodiment of the invention according to FIG. 1, a voice prosthesis 1000 is disclosed. The voice prosthesis 1000 comprises a lateral tubular body 100. The tubular body 200 has a distal and a proximal axial end. The proximal end is intended to be facing the esophagus of the user, and the distal end is intended to be facing the trachea, during use. The proximal end is provided with a esophageal retention flange 101. The distal end is provided with a tracheal retention flange 102. The esophageal and tracheal retention flanges 101 and 102 are arranged to extend laterally outwards from the lateral tubular body 100 in a plane being transversal to a central axis of the tubular body. The lateral tubular body 100 is manufactured in a flexible plastic or rubber material, such as silicone. When the lateral tubular body 100 is manufactured in silicone, allergic reactions with the patient tissue may be decreased.

Inside, i.e. in the lumen of the lateral tubular body 100, a valve member 200 is arranged, said valve member 200 being suitable for closing the communication through the lateral tubular body 100 but opens when subjected to air flow in the proximal direction. Air flow in the proximal direction is realised by the user when he/she exhales at the same time as he/she occludes the stoma with his/her hand/finger or by activating a tracheostoma valve arranged to cover the stoma.

The valve member 200 comprises a valve disc 201 and a valve seat 202. The valve disc 201 and the valve seat 202 are arranged in a tubular valve body 203. The valve disc 201 is arranged on a valve flap 204, which in turn connects the valve disc 201 to the valve body 203. The valve member 200 is adapted to engagingly fit within the lateral tubular body 100, such that air or liquid does not pass circumferentially of the valve member 200. To facilitate such cooperation between the central lumen wall of the lateral tubular body 100, a retaining rim 103 is arranged in the lumen of the lateral tubular body 100, said retaining rim 103 extending centrally. In a corresponding way, the valve member 200 is provided with a laterally extending proximal rim 205, which is adapted to cooperate with the retaining rim 103 in a manner that will assure correct positioning of the valve member 200 in the lumen of the lateral tubular body 100, by inserting the valve member 200 until it hits and is stopped by the interaction between the retaining rim 103 of the lateral tubular body 100 and the proximal rim 205 of the valve member 200.

The valve disc 201 and the valve seat 202 are manufactured in a rigid candida resistant material, such as a fluorine polymer or a metal. An example of a suitable fluorine polymer is polyvinylidene difluoride (PVDF). Examples of candida resistant metals are stainless steel and titanium.

The valve seat 202 is arranged circumferentially of the lumen of the valve body 203. The valve seat 202 may also be arranged in a plane that is traversing the lumen of the valve body 203 and is angled in relation the transversal plane of the valve body 203. In this way the surface area of the valve disc 201 may be increased, such that the lifting force from exhalation may be increased. This in turn gives that the closing force of the valve disc through the valve flap 204 may be increased, decreasing the risk of unwanted leakage from the esophagus into the trachea. When the valve disc 201 is connected to the valve body 203—via the valve flap 204—such that the valve flap 204 extends proximocentrally from the wall of the valve body 203, the valve flap 204 may be provided with a pre-stress. In this way, the closing force of the valve flap 204 may be increased.

The valve flap 204 may be manufactured in a suitable elastic material with good flexibility memory, such that the closing force will be adequately maintained for a long period of time. As suitable such elastic material is silicone. Also, when the valve flap 204 is arranged in a through hole in the wall of the valve body 203, and the valve flap 204 and the lateral tubular body 100 both are of silicone, such that the lateral part of the valve flap 204 interacts with the lumen of the tubular body 100, a chemical adherence between the valve flap 204 and the tubular body 100 occurs, which will further improve the sealing effect between the valve member 200 and the tubular body 100.

On the distal side the valve disc 201 is provided with sealing rim 206. The sealing rim 206 abuts the valve seat 202 when the valve member 200 closes the passage through the valve member 200, and thus also closes the passage through the voice prosthesis 1000. The sealing rim 206 ensures that the interaction area between the valve disc 201 and the valve seat 202 is kept small, and that the candida accessibility to the interaction area is kept as low as possible. When the interaction area is distanced from the valve disc 201 through the arrangement of the sealing rim 206, the candida will much rather gather at the base of the rim 206 towards the disc 201, and on the central parts of the disc 201, such that only an extremely severe candida growth will end up affecting the interaction area. Such severe candida growth will almost never happen when the valve disc 201, and thus the rim 206, is made of a candida resistant material, which is envisioned in accordance with above. Additionally, due to the rim 206, the interaction area between the valve disc 201 and the valve seat 202 may be kept small, thus decreasing the risk of candida/mucus/food interference. Still further, even if candida/mucus/food ends up at the interface area, the rim 206 will more likely to overcome said candida/mucus/food, due to a higher pressure/area unit, thus increasing the ability to seal off the trachea from the esophagus.

In an alternative embodiment, the rim 206 is arranged on the valve seat 202 instead of the valve disc 201.

The rim 206 may be wedge-shaped in cross-section along a longitudinal plane. In this way, the interaction area between the valve disc 201 and the valve seat 202 is delimited to the peak circumference of the wedge-shaped rim 206, and thus further increasing the force per area unit and further decreasing the risk of candida/mucus/food getting caught at the interaction area.

The height of the rim 206 may be 0.15 mm or above, to make sure that enough distance is created to significantly lower the risk of eventual candida/mucus/food on the valve disc 201 to interact with the interaction area between the valve disc 201 and the valve seat 202. In practice, the height of the rim 206 is 0.15 to 1.5 mm, such as 0.2 to 1 mm.

The rim 206 may be a separate ring member that is brought into cooperation, through gluing or snap-in fitting, with the valve disc 201, or it may of course be monolithically integrated with the valve disc 201. For example, if the valve disc 201 is made of a polymer, such as a candida resistant polymer, in accordance with above, the rim 206 may be a metal ring, such as a stainless steel or titanium ring, that is brought into cooperation with the valve disc 201. Naturally, the opposite choice of materials also apply. Alternatively, the rim 206 is monolithically integrated with the valve disc 201 in a candida resistant material, such as a candida resistant polymer or metal in accordance with above.

Distally of the valve seat 202, the valve member 200 is provided with through holes 207 in the tubular wall thereof. These through holes 207 realise injection of glue from the lumen of the valve member 200, through the through holes 207, into a cavity 208 between the valve member 200 and the tubular body 100, once the valve member 200 has been positioned correctly within the lumen of the tubular body 100. In this way, there will be no need of injecting glue circumferentially of the valve member 200 subsequent, prior or during placement of the valve member 200 in the tubular body 100. Instead, an anvil—holding the valve member 200 for insertion thereof in the tubular body 100—may be provided with holding taps that interact with through holes 207 in a retaining manner, said taps also being glue outlets. In this way, the arrangement of the valve member 200 in the tubular body 100 is facilitated, while simultaneously avoiding the risk of undue and cumbersome glue injection between the different parts.

Thus, the present invention envisions the insertion of a valve member 200 into the tubular body 100, where after glue is injected through the through holes 207 into a space in between the valve member 200 and the tubular body 100. Thereafter, the glue is cured. Subsequently, the anvil, holding the valve member 200 during insertion into the tubular body 100 and during injection of glue, is withdrawn.

In accordance with FIG. 3, one (or several) permanent magnet(s) 300 may be provided in the proximity of the valve disc 201 and may be connected with the valve disc 201 or the valve flap 204 by gluing or by being moulded into the material at injection moulding of the valve disc 201 or the valve flap 204, respectively. In a corresponding way, the valve seat 202 may be provided with a magnetically attractable material 301, such that the valve disc 201 or valve flap 204, respectively, by magnetic force normally is held in closed position, thus realizing sealing engagement between the valve disc 201, via the rim 206, and the valve seat 202, but can be lifted momentarily from the seat by an overpressure in trachea overcoming the magnet force. In a modification of the embodiment shown, the magnet (or several) magnet(s) 300 is provided in the valve seat 202 while the valve disc 201 or the valve flap 204, respectively, comprises a magnetically attractable material 301. In order that the magnet(s) 300 shall be protected against corrosion it can be coated with a corrosion resistant material.

The elements and components of an embodiment of the invention may be physically, functionally and logically implemented in any suitable way. Indeed, the functionality may be implemented in a single unit, in a plurality of units or as part of other functional units.

Although the present invention has been described above with reference to specific embodiments, it is not intended to be limited to the specific form set forth herein. Rather, the invention is limited only by the accompanying claims and, other embodiments than the specific above are equally possible within the scope of these appended claims.

In the claims, the term "comprises/comprising" does not exclude the presence of other elements or steps. Furthermore, although individually listed, a plurality of means, elements or method steps may be implemented by e.g. a single unit or processor. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc do not preclude a plurality. Reference signs in the claims are provided merely as a clarifying example and shall not be construed as limiting the scope of the claims in any way.

The invention claimed is:

1. A voice prosthesis for mounting in a fistula between a trachea and an esophagus, comprising:
   a tubular body having a lumen about a central axis, the tubular body including an esophageal retention flange and a tracheal retention flange extending transverse to the central axis; and
   a valve member including a valve disc and a valve seat, the valve member being arranged in the lumen of the tubular body while forming a cavity between an outermost surface of the valve member and an inner surface of the tubular body, the valve disc and the valve seat controlling flow through the lumen by interaction between the valve disc and the valve seat,
   wherein the valve member further includes a tubular wall with a through hole positioned distally from the valve seat, the through hole being in fluid communication with the cavity,
   wherein the valve disc includes a sealing rim having a wedge shaped protrusion configured to contact the valve seat,
   wherein the interaction between the valve disc and the valve seat is obtained via the sealing rim, and
   wherein the valve disc is provided with the sealing rim, such that the sealing rim abuts the valve seat when the interaction between the valve disc and the valve seat closes a passage through the tubular body.

2. The voice prosthesis according to claim 1, wherein the sealing rim of the valve disc is wedge-shaped in cross-section along a longitudinal plane of the tubular body.

3. The voice prosthesis according to claim 1, wherein the height of the sealing rim of the valve disc is 0.15 mm or above.

4. The voice prosthesis according to claim 1, wherein the height of the sealing rim of the valve disc is 0.15 to 1.5 mm.

5. The voice prosthesis according to claim 1, wherein the tubular body incudes a distal axial end and a proximal axial end, wherein the proximal axial end is provided with the esophageal retention flange and the distal axial end is provided with the tracheal retention flange.

6. The voice prosthesis according to claim 5, wherein the esophageal and tracheal retention flanges are arranged to extend laterally outwards from the tubular body in a plane being transversal to a central axis of the tubular body.

7. The voice prosthesis according to claim 1, wherein the tubular body is manufactured of silicone.

8. The voice prosthesis according to claim 1, wherein the through hole is configured to retain a corresponding tap of an anvil.

9. The voice prosthesis according to claim 1, wherein the through hole is configured to allow glue injection into the cavity.

10. The voice prosthesis according to claim 8, wherein the valve disc is arranged on a valve flap, which in turn connects the valve disc to the tubular valve body.

11. The voice prosthesis according to claim 10, wherein the valve flap is manufactured of silicone.

12. The voice prosthesis according to claim 1, wherein the valve disc includes the wedge shaped protrusion, and the valve seat is manufactured of fluorine polymer.

13. The voice prosthesis according to claim 1, wherein the valve seat is arranged circumferentially of the lumen of the tubular body, in a plane traversing the lumen of the tubular body, the plane being angled in relation the transversal plane of the tubular body.

14. The voice prosthesis according to claim 1, wherein the valve disc extends proximally and centrally from the wall of the tubular body.

15. The voice prosthesis according to claim 1, wherein at least one permanent magnet is provided in the proximity of the valve disc, and a magnetically attractable material is provided in the proximity of the valve seat, such that the sealing rim of the valve disc by a magnetic force is held in a closed position, but the sealing rim including the wedge shaped protrusion can be lifted momentarily from the valve seat by an overpressure in the trachea overcoming the magnetic force.

16. The voice prosthesis according to claim 1, wherein at least one permanent magnet is provided in the proximity of the valve seat, and a magnetically attractable material is provided in the proximity of the valve disc, such that the sealing rim of the valve disc by a magnetic force is held in a closed position, but the sealing rim including the wedge shaped protrusion can be lifted momentarily from the valve seat by an overpressure in the trachea overcoming the magnetic force.

17. The voice prosthesis of claim 1, wherein the tubular body incudes a distal axial end and a proximal axial end, and the cavity extends in an axial direction along the lumen of the tubular body and between the distal axial end and the proximal axial end.

18. A voice prosthesis comprising:
   a tubular body having a lumen about a central axis, the tubular body including an esophageal retention flange and a tracheal retention flange extending transverse to the central axis; and
   a valve member configured to be arranged in the lumen of the tubular body while forming a cavity between an outermost surface of the valve member and an inner surface of the tubular body and that extends in an axial direction along the lumen of the tubular body, the valve member including a valve seat and a valve disc having a wedge shaped protrusion configured to contact the valve seat, and
   wherein the valve member further includes a tubular wall with a through hole positioned distally from the valve seat, the through hole being in fluid communication with the cavity.

19. The voice prosthesis of claim 18, wherein the tubular body incudes a distal axial end and a proximal axial end, and the cavity extends in the axial direction along the lumen of the tubular body and between the distal axial end and the proximal axial end.

20. The voice prosthesis of claim 18, wherein the through hole is configured to allow glue injection into the cavity.

* * * * *